US007456304B2

(12) United States Patent
Lee et al.

(10) Patent No.: US 7,456,304 B2
(45) Date of Patent: Nov. 25, 2008

(54) METHOD FOR IMPROVING CONVERSION RATE OF OIL SOLUBLE UNSATURATED LIPIDS INTO WATER-SOLUBLE LIPIDS

(75) Inventors: Seong Kweon Lee, Daejeon-si (KR); Soon-Kee Sung, Daejeon-si (KR); Sung Soo Kim, Daejeon-si (KR); Jung Kyu Yi, Daejeon-si (KR)

(73) Assignee: Dongbu Hannong Chemical Co., Ltd., Seoul (KR)

( * ) Notice: Subject to any disclaimer, the term of this patent is extended or adjusted under 35 U.S.C. 154(b) by 292 days.

(21) Appl. No.: 11/388,417

(22) Filed: Mar. 24, 2006

(65) Prior Publication Data

US 2006/0228322 A1    Oct. 12, 2006

(30) Foreign Application Priority Data

Apr. 11, 2005    (KR) .................. 10-2005-0029828

(51) Int. Cl.
*C07C 227/00* (2006.01)

(52) U.S. Cl. .................. 554/114; 424/70.22

(58) Field of Classification Search .................. None
See application file for complete search history.

(56) References Cited

OTHER PUBLICATIONS

W.M.N. Ratnayake, et al., Preparation of Omega-3 PUFA Concentrates From Fish Oils Via . . . , Fat Sci. Technol., 90 pp. 381-386, 1988.
N. Haagsma, et al., Preparation of an w3 Fatty Acid Concentrate From Cod Liver Oil, JAOCS, 59, pp. 117-118, 1982.

*Primary Examiner*—Deborah D Carr
(74) *Attorney, Agent, or Firm*—Lucas & Mercanti, LLP

(57) ABSTRACT

Disclosed relates to a method for improving a conversion rate of oil soluble unsaturated lipids into water-soluble lipids and, more particularly, to a method for improving a conversion rate of oil soluble unsaturated lipids into water-soluble lipids that forms an unsaturated lipid-chloride derivative having an increased reaction activity by using a pyridine-thionyl chloride as a catalyst, not directly causing a reaction between the unsaturated lipids and amino acids, or that applies an emulsifier to cause a reaction between the unsaturated lipids and amino acids so as to minimize the size of lipid particles to a nano-size of less than 50 nm, thus improving the reaction conversion rate to more than 99%.

22 Claims, 1 Drawing Sheet

METHOD FOR IMPROVING CONVERSION RATE OF OIL SOLUBLE UNSATURATED LIPIDS INTO WATER-SOLUBLE LIPIDS

This patent application claims the benefit of priority from Korean Patent Application No. 10-2005-0029828 filed Apr. 11, 2005, the contents of which are incorporated herein by reference.

BACKGOUND OF THE INVENTION

1. Field of the Invention

The present invention relates to a method for improving a conversion rate of oil soluble unsaturated lipids into water-soluble lipids.

2. Description of Related Art

Unsaturated lipids exist in the form of water-soluble lipoprotein in a human body that has essential efficacies for anticancer, anti-inflammatory (atopy skin diseases), anti-obesity, prevention of dementia, improvement of eyesight, treatment for cardiovascular diseases and the like. That is, the unsaturated lipid is composed of a mixture of lipid and protein or amino acid. Among these compositions, if the amount of low-density lipoprotein and neutral lipid are increased, various diseases such as cardiovascular diseases may break out.

Accordingly, to prevent and treat such diseases, various researches aimed at taking in unsaturated fatty acids in a high purity have been made actively and obtained desired results.

However, since the unsaturated fatty acids exist in the form of oil soluble lipids, not dissolved in water, including fatty acid, fatty acid ester, neutral lipid such as triglyceride, etc., it is impossible to inject such unsaturated fatty acids directly into the blood. Accordingly, unsaturated fatty acids are being taken in the form of soft capsules or taken by drinking.

To solve the above described problems, numerous researches aimed at converting oil soluble lipids into water-soluble lipids have continued to progress.

First, a method for salifying oil soluble lipids using alkali metal salts such as Na, K, Ca, etc. has been studied. This method, however, has a serious problem in applying the salified lipids to the human body since they existing as a strong alkaline in an aqueous solution are toxic and irritative.

Second, a method for microencapsulating oil soluble lipids using an emulsifier, dextrine and milk protein has been studied. However, this method is attended with a restriction that the emulsifier should have biocompatibility and excellent solubility and, at the same time, requires a higher stability for environment such as heat and light.

Besides, Korean Patent Application No. 10-2003-30853 has disclosed a water-soluble lipid complex containing a basic amino acid and a method for preparing the same. According to the method, unsaturated lipids and basis amino acids react directly with each other. However, since all of the amino acids existing in nature, such as acidic, neutral, aromatic amino acids, etc., except for the basic amino acids, cannot react directly with the unsaturated lipids, specifically with fatty acids, only the basic amino acids, which can react with fatty acids, are subject to the reaction. Besides, although the lipid complex prepared according to the above-described method has better solubility and absorptiveness than the microencapsulating method, it has still a problem of irritating human body since it uses the basic amino acids the same with the above-described method for salifying oil soluble lipids using alkali metal salts. Moreover, the above method has an additional disadvantage in view of the oxidative stability since the unsaturated lipids are oxidized by heat, air and light and are decomposed by adding acids when converting the unsaturated lipids to neutral or weakly acidic formulations for the purpose of applying them as raw materials for food, pharmaceutical and cosmetic uses. In addition, the above method still has a defect that it is impossible to dissolve water and oil completely on a molecular level to react with each other since it should cause reaction at a sustained stirring rate of 2000 rpm by adding oil soluble fatty acids slowly to an aqueous solution in which basic amino acids are completely dissolved. Accordingly, unreacted fatty acids are always left in the reactant and reduce safety and stability of oil soluble fatty acids, thus resulting in noxious materials that deteriorate the quality of end products in a mass production.

Accordingly, the inventors of the preset invention have tried to find a method for converting the remaining unreacted unsaturated lipids in the reactant into water-soluble lipids and complete the present invention that can convert unsaturated lipids into water-soluble lipids at least 99% having excellent safety and stability by causing a reaction in optimum conditions where all unsaturated lipids can be bound with all amino acids.

SUMMARY OF THE INVENTION

Accordingly, an object of the present invention is to provide a method for improving a conversion rate of oil soluble unsaturated lipids, specifically fatty acids, into water-soluble lipids.

The method of the invention includes a process using catalysts and a process using emulsifiers.

First, a method for improving a conversion rate of oil soluble unsaturated lipids into water-soluble lipids using catalysts comprises the steps of:

(1-1) putting an oil soluble unsaturated lipid into a pyridine to be completely dissolved and adding a thionyl chloride by split injections to the resulting solution to form an unsaturated lipid-chloride derivative;

(1-2) adding the unsaturated lipid-chloride derivative formed in step (1-1) to a solution, in which a dehydrated ethanol and an amino acid are dissolved, to react under the presence of a catalyst, thus forming a water-soluble lipid complex; and (1-3) removing the ethanol from the resulting solution formed in step (1-2) by vacuum drying, putting water into the reactant to be solubilized and, then, collecting the water-soluble lipid complex using a lyophilizer.

Second, a method for improving a conversion rate of oil soluble unsaturated lipids into water-soluble lipids using emulsifiers comprises the steps of:

(2-1) stirring an oil soluble unsaturated lipid with water at a stirring rate of 3,000 to 7,000 rpm keeping a temperature within 4° C. to −1° C. and, adding an emulsifier to the resulting solution to be emulsified;

(2-2) adding an amino acid to the emulsified solution obtained in step (2-1) to form a water-soluble lipid complex; and (2-3) collecting the water-soluble lipid complex from the resulting solution formed in step (2-2) using a lyophilizer.

Besides, the method for improving the conversion rate of oil soluble unsaturated lipids (specifically, neutral lipids) into water-soluble lipids in accordance with the present invention, including a process using catalysts and a process using emulsifiers, comprises the steps of:

(3-1) mixing an oil soluble unsaturated lipid, water, ethanol, sodium hydroxide and phosphoric acid to form two phases;

(3-2) removing a subnatant of the resulting solution formed in step (3-1), putting a pyridine into a supernatant of the resulting solution to be completely dissolved and adding a thionyl chloride by split injections to the resulting solution to form an unsaturated lipid-chloride derivative;

(3-3) putting the unsaturated lipid-chloride derivative formed in step (3-2) into a dehydrated ethanol, stirring the resulting solution at a stirring rate of 3,000 to 7,000 rpm keeping a temperature within 4° C. to −1° C. and, adding an emulsifier to the resulting solution to be emulsified;

(3-4) adding an amino acid into the emulsified solution obtained in step (3-4) to form a water-soluble lipid complex by causing a reaction with the resulting solution under the presence of a catalyst; and (3-5) removing the ethanol from the resulting solution formed in step (3-4) by vacuum drying, putting water into the reactant to be solubilized and, then, collecting the water-soluble lipid complex using a lyophilizer.

The methods of the invention described above will be described in steps hereinafter.

In step (1-1), unsaturated lipids are completely dissolved in pyridine and, thionyl chloride is added by split injections to the resulting solution at 4° C. If not adding thionyl chloride by split injections, the reaction proceeds rapidly and, accordingly, the rancidity of the unsaturated lipids proceeds severely. Adding thionyl chloride by split injections to the resulting solution to be stirred for about forty minutes results in forming crystals. The resulting solution containing such crystals is stationed at room temperature for about two hours and, then, filtered to obtain unsaturated lipid-chloride derivatives in the form of crystals. According to the method of the invention, unsaturated lipids are not subject to react directly with amino acids; whereas, the invention forms unsaturated lipid-chloride derivatives, thus increasing the activity of reaction.

In step (1-2), the unsaturated lipid-chloride derivatives formed in step (1-1) are put into a solution, in which dehydrated ethanol and amino acid are dissolved, to react at 4° C. Then, pyridine and thionyl chloride as catalysts in the ratio of 1:1 are added to the resulting solution. As a result, solid particles existing in the solution are dissolved to form amino acid-unsaturated lipid complexes.

In step (1-3), at the very point of time when the resulting solution prepared in step (1-2) becomes clear, the reaction is terminated. Then, ethanol is removed from the solution using a rotary vacuum evaporator and, water is put into the reactant to be solubilized. Water-soluble lipid complexes are obtained using a lyophilizer.

In step (2-1), oil soluble unsaturated lipids and water are stirred at a stirring rate of 3,000 to 7,000 rpm, preferably more than 5,000 rpm, keeping the temperature within 4° C. to −1° C., preferably 4° C. Then, an emulsifier is added to the resulting solution to be emulsified in order to completely dissolve the oil soluble unsaturated lipids and water and, to enhance the stability of the resulting solution. If adding the emulsifier, the size of lipid particles becomes smaller, 50 nm or less, which minimizes the interfacial tensions and maximizes the surface areas, thus improving the conversion rate up to 99% or more. Here, the emulsifier applied in this step includes 1.0 to 3.0 weight % of lecithin, 1.0 to 3.0 weight % of sucrose fatty acid ester and 0.02 to 0.08 weight % of ascorbic acid to a total weight of the solution and, preferably includes 2.0 weight % of lecithin, 2.0 weight % of sucrose fatty acid ester and 0.05 weight % of ascorbic acid to a total weight of the solution.

In step (2-2), amino acids are added slowly to the emulsified solution obtained in step (2-1) to form water-soluble lipid complexes. Here, if adding much amino acid at a time, a sudden reaction is made to increase the viscosity of the reactant, thus obstructing a smooth stirring. That is, if so, the reactant turns into a suddenly solidified state like jelly so as not to convert the reactant into water-soluble lipids completely, thus not avoiding the problem of toxicity in the body due to lack of oxidative stability.

In step (2-3), water-soluble lipid complexes are collected from the resulting solution formed in step (2-2) using a lyophilizer.

The unsaturated lipids applied to a method for improving a conversion rate of oil soluble unsaturated lipids into water-soluble unsaturated lipids in accordance with the present invention include fatty acid, neutral lipid, fatty acid ester and steroid. Here, the fatty acid applied is preferably unsaturated fatty acid having 10 to 30 carbon atoms and 1 to 6 bonds and, more preferably, is at least one selected from the group consisting of a myristoleic acid, a palmitoleic acid, a γ-linolenic acid, an α-linolenic acid, an oleic acid, a linoleic acid, a conjugated linoleic acid, a docosahexaenoic acid (DHA) and an eicosapentaenoic acid (EPA).

The unsaturated fatty acids applied to the present invention include foods containing the same. For example, the unsaturated fatty acids include general evening primrose oil or refined fish oil containing oleic acid or linoleic acid.

Besides, the amino acid applied to a method for improving a conversion rate of oil soluble unsaturated lipids into water-soluble unsaturated lipids in accordance with the present invention is at least one selected from the group consisting of essential amino acid and nonessential amino acid: the essential amino acid consisting of isoleucine, leucine, lysine, phenylalanine, methionine, threonine, trytophane and valine; and the nonessential amino acid consisting of alanine, arginine, asparagines, cysteine, glutamine, histidine, proline, serine, tyrosine and glycine, however, not limited hereto.

As a result of measuring the formation of water-soluble complex in accordance with the present invention using an infrared analyzer, the carboxylate ion ($COO^-$) peaks of the water-soluble complex are shown at 1560 $cm^{-1}$ and 1395 $cm^{-1}$ as depicted in FIG. 1.

In addition, since peroxide values of the water-soluble lipid complex in accordance with the present invention are shown lower than those prepared according to the conventional method and DHA oils, the water-soluble lipid complex obtained according to the invention has an excellent stability as depicted in FIG. 2.

The method for improving the conversion rate of oil soluble unsaturated lipids into water-soluble lipids in accordance with the present invention improves the safety under the acidic and basic conditions, attenuates the toxicity, enhances the stability for environment factors such as heat, air and light and, at the same time, increases the absorptiveness in the body and the solubility in water remarkably, thus facilitating administration and absorption in the body. Moreover, the water-soluble lipid complex prepared in the manner described above can be applied for the uses of injection, eating and drinking, syrup, water-soluble cream and lotion, etc. in various fields of medicine, health food, and functional cosmetics.

DETAILED DESCRIPTION OF THE INVENTION

Hereinafter, preferred embodiments of the present invention will be described in detail with reference to the attached drawings. The present invention is not restricted to the following embodiments, and many variations are possible within the spirit and scope of the present invention. The embodiments of the present invention are provided in order to more completely explain the present invention to anyone skilled in the art.

Embodiment 1

Method for Preparing Water-Soluble Lipid Complex from Fatty Acids Using Catalysts 1. Preparation of Conjugated Linoleic Acid-Chloride Derivatives After putting 100 g of conjugated linoleic acid (80%) into 50 ml of pyridine to be completely dissolved, 50 ml of thionyl chloride was added by spilt injections to the resulting solution at 4° C. If not adding thionyl chloride by split injections, the reaction proceeds rapidly, thus not avoiding the rancidity of conjugated linoleic acid. Adding thionyl chloride by split injections to the resulting solution to be stirred for about forty minutes resulted in forming crystals. Then, the resulting solution containing such crystals was stationed at room temperature for about two hours and, then, filtered to obtain conjugated linoleic acid-chloride derivatives in the form of crystals.

2. Preparation of Glycine-Conjugated Linoleic Acid Complexes 100 g of the conjugated linoleic acid-chloride was put into a solution, in which 1 L of dehydrated ethanol and 50 g of Glycine were dissolved, to react at 4° C. Then, each 50 ml of pyridine and thionyl chloride as catalysts in the ratio of 1:1 were added to the resulting solution. As a result, solid particles existing in the solution were dissolved to form Glycine-conjugated linoleic acid complexes. At the very point of time when the resulting solution became clear, the reaction was terminated. Next, ethanol was removed from the solution using a rotary vacuum evaporator and, 100 ml of water was put into the reactant to be solubilized. Consequently, 143 g of water-soluble complexes were obtained using a lyophilizer. The process of forming water-soluble complex was measured using an infrared analyzer and the result is depicted in FIG. 1.

Figure 1:
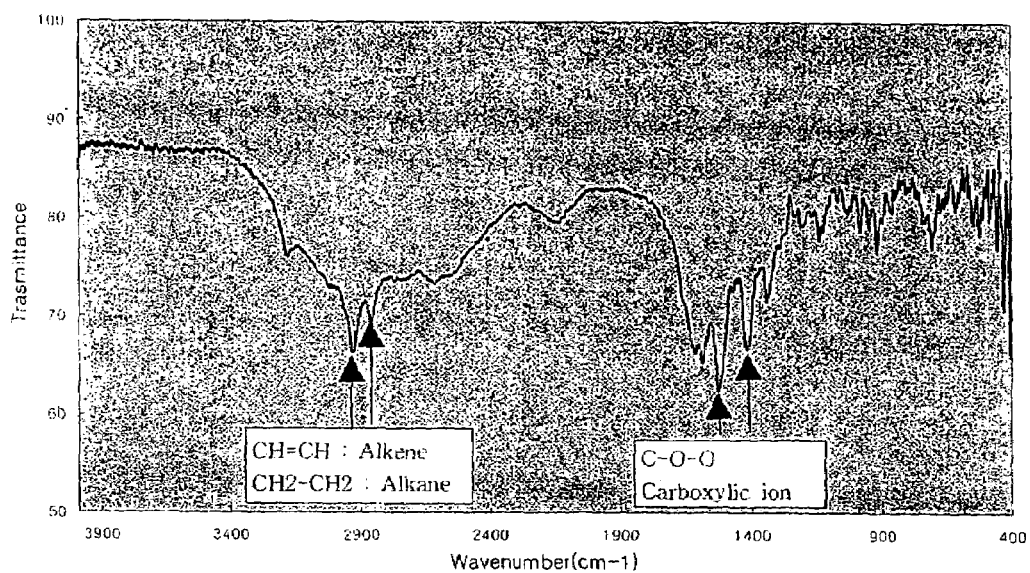
FIG. 1 is a coloured graph illustrating the formation water-soluble lipid complex in accordance with the present invention with an infrared spectrum.

As shown in FIG. 1, it was found that the carboxylate ion ($COO^-$) peaks of the water-soluble complex are shown at 1560 $cm^{-1}$ and 1395 $cm^{-1}$.

Embodiment 2

Method of Preparing Water-Soluble Lipid Complexes from Fatty Acids Using Catalysts 1. Preparation of DHA-Chloride Derivatives DHA-chloride derivatives were obtained in the form of crystals using DHA instead of the conjugated linoleic acids in the same manner in step 1 of Embodiment 1.

2. Preparation of Lysine-DHA Complexes

Lysine was used instead of Glycine in step 2 of Embodiment 1 and, 3 ml, instead of 5 ml, of pyridine and thionyl chloride in the ratio of 1:1 was added to the resulting solution to form DHA-chloride derivatives in the same manner in step 2 of Embodiment 1, thus collecting 139 g of water-soluble complexes.

The water-soluble complex obtained in the above process was measured using an infrared analyzer and the result is depicted in FIG. 1.

As shown in FIG. 1, it was found that the carboxylate ion ($COO^-$) peaks of the water-soluble complex are shown at 1560 $cm^{-1}$ and 1395 $cm^{-1}$.

Embodiment 3

Another Method of Preparing Water-Soluble Lipid Complexes from Fatty Acids Using Emulsifiers 200 mg of conjugated linoleic acid and 1 L of water were stirred at a stirring rate of 5,000 rpm keeping the temperature 4° C. and, an emulsifier including 2.0 weight % of lecithin, 2.0 weight % of sucrose fatty acid ester and 0.05 weight % of ascorbic acid to a total weight of the solution was added to the resulting solution to be emulsified. Then, mixed powder of 100 g of Glycine and 100 g of lysine was slowly added to the reactant, keeping the reaction conditions of 4° C. and 5,000 rpm till the reactant became a homogenous phase. At the very point of time when the resulting solution became clear, the reaction was terminated. As a result, 393 g of water-soluble complexes were obtained using a lyophilizer.

The water-soluble complex obtained during the above process was measured using an infrared analyzer and the result is depicted in FIG. 1.

As shown in FIG. 1, it was found that the carboxylate ion ($COO^-$) peaks of the water-soluble complex are shown at 1560 $cm^{-1}$ and 1395 $cm^{-1}$.

Embodiment 4

Method of Preparing Water-Soluble Lipid Complexes from Neutral lipids 100 g of borage oil (gamma linoleic acid 20%), water and ethanol each having the same weight % were stirred at a stirring rate of 3,000 rpm, into which 40 g of sodium hydroxide was put. Next, when 60 g of phosphoric acid were added to the reactant, two phases were formed. After removing the subnatant, 50 ml of pyridine was added to the supernatant of the resulting solution and, then, thionyl chloride was added by split injections to the resulting solution to be stirred at 4° C. for about forty minutes. As a result, crystals were formed in the resulting solution. After stationing the resulting solution containing such crystals at room temperature for about two hours, the resulting solution was filtered to obtain gamma linoleic acid-chloride derivatives in the form of crystals. The obtained gamma linoleic acid-chloride derivatives were put into 1 L of dehydrated ethanol to be stirred at a stirring rate of 5,000 rpm and at a temperature of 4° C. Here, 2.0 weight % of lecithin, 2.0 weight % of sucrose fatty acid ester and 0.05 weight % of ascorbic acid to a total weight of the solution were put into the mixing solution to emulsify the solid phase in the solution. Subsequently, amino acid mixed powders consisting of Glycine, phenylalanine and lysine (50 g each) were slowly added to the resulting solution and 10 ml of solution of a pyridine and a thionyl chloride in the ratio of 1:1 were added by split injections to the resulting solution, keeping the reaction conditions of 4° C. and 5,000 rpm till the reactant became a homogenous phase. At the very point of time when the resulting solution became clear, the reaction was terminated. As a result, 240 g of water-soluble complexes were obtained by removing ethanol using a rotary vacuum evaporator and by drying the reactant using a lyophilizer.

The water-soluble complex obtained during the above process was measured using an infrared analyzer and the result is depicted in FIG. 1.

As shown in FIG. 1, it was found that the carboxylate ion (COO⁻) peaks of the water-soluble complex are shown at 1560 cm$^{-1}$ and 1395 cm$^{-1}$.

EXPERIMENTAL EXAMPLE

Method of Measuring Peroxide Values (AOCS Method)

An experiment, which will be described below, was carried out to identify the peroxide values of the water-soluble lipid complexes in accordance with the present invention.

2 g of water-soluble complex prepared according to Embodiment 1 were put into a 250 ml Erlenmeyer flask and 20 ml of mixed solvent of acetic acid/chloroform (3/2 (v/v)) was added therein to be dissolved. Next, 0.5 ml of saturated KI solution was put into the resulting solution, and, then, the reaction flask was left in a dark room for one minute. After pulling the flask out of the dark room, 20 ml of distilled water was added to the solution and, then, starch indicator was put into the resulting solution. To obtain peroxide values, the solution was titrated with 0.01N sodium thiosulfate till the purple color of the solution turned into colorlessness. Peroxide values were calculated as following mathematic formula 1 and the result is depicted in FIG. 2.

[Formula 1]

Peroxide Value=[(S−B)×100]/W, wherein S represents an titrated value of sample; B expresses an titrated value of blank; and W denotes a size of sample.

Figure 2:
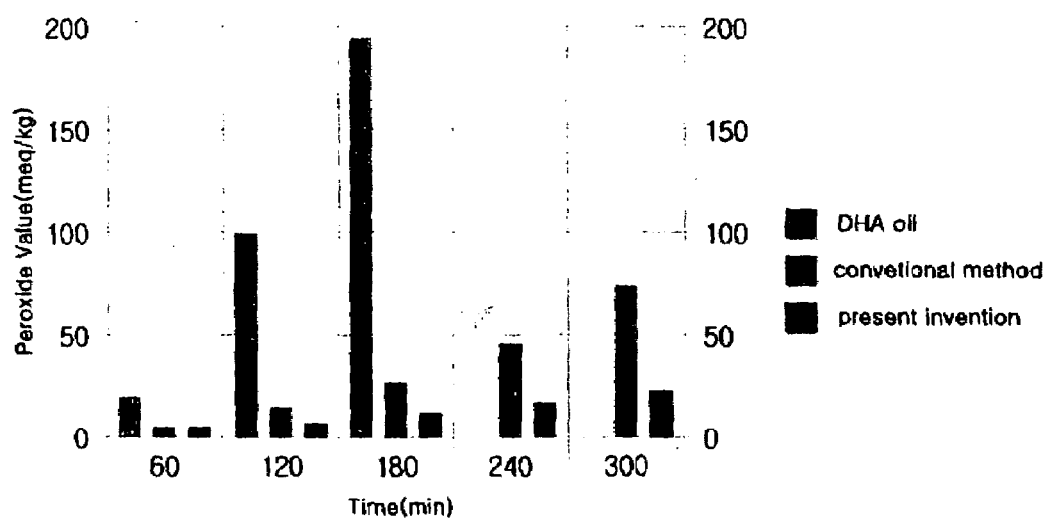
FIG. 2 is a coloured graph depicting peroxide values of water-soluble lipid complex in accordance with the present invention measured by minutes.

As shown in FIG. 2, the peroxide values of water-soluble lipid complex in accordance with the present invention were measured lower than those of DHA oil and those of water-soluble complex prepared according to the conventional method. Accordingly, it can be known that the present invention provides water-soluble lipid complex having an excellent stability.

Besides, the method of the present invention improves the safety under the acidic and basic conditions, attenuates the toxicity, enhances the stability for environment factors such as heat, air and light and, at the same time, increases the absorptiveness in the body and the solubility in water remarkably, thus facilitating administration and absorption in the body.

Moreover, the water-soluble lipid complex prepared in a manner described above can be applied for the uses of injection, eating and drinking, syrup, water-soluble cream and lotion, etc. in various fields of medicine, health, food, and functional cosmetics.

What is claimed is:

1. A method for improving a conversion rate of oil soluble unsaturated lipid into water-soluble unsaturated lipid comprising:
   (1-1) dissolving an oil soluble unsaturated lipid in a pyridine;
   (1-2) adding a thionyl chloride by split injections to the resulting solution from step (1-1) to form an unsaturated lipid-chloride derivative;
   (1-3) adding the unsaturated lipid-chloride derivative found in step (1-2) to a solution containing dehydrated ethanol and an amino acid to form an amino acid-unsaturated lipid complex in the presence of a pyridine and a thionyl chloride as a catalyst;
   (1-4) removing the ethanol from the resulting solution formed in step (1-3) by vacuum drying; and
   (1-5) dissolving a water-soluble unsaturated lipid complex resulting from step (1-4) in water and collecting the water-soluble unsaturated lipid complex using a lyophilizer.

2. A method for improving a conversion rate of oil soluble unsaturated lipid into water-soluble unsaturated lipid comprising:
   (2-1) mixing an oil soluble unsaturated lipid with water at a stirring rate of 3,000 to 7,000 rpm at a temperature of 4° C. −1° C.;
   (2-2) adding a lecithin, a sucrose fatty acid ester and an ascorbic acid as an emulsifier to the resulting solution from step (1-1) to form an emulsion solution;
   (2-3) adding an amino acid to the emulsion solution obtained in step (2-2) to form an amino acid-unsaturated lipid complex; and
   (2-4) collecting a water-soluble unsaturated lipid complex using a lyophilizer.

3. A method for improving a conversion rate of oil soluble unsaturated lipids into water-soluble unsaturated lipids comprising:
   (3-1) mixing an oil soluble unsaturated lipid, water, ethanol, sodium hydroxide and phosphoric acid to form two phases;
   (3-2) dissolving a supernatant of the resulting solution formed in step (3-1) in a pyridine;
   (3-3) adding a thionyl chloride by split injections to the resulting solution from step (3-2) to form an unsaturated lipid-chloride derivative;
   (3-4) mixing the unsaturated lipid-chloride derivative with dehydrated ethanol at a stirring rate of 3,000 to 7,000 rpm at a temperature of 4° C. to −1° C.;
   (3-5) adding a lecithin, a sucrose fatty acid ester and an ascorbic acid to form an emulsion solution;
   (3-6) adding an amino acid into the emulsion solution obtained in step (3-5) to form an amino acid-unsaturated lipid complex in the presence of a pyridine and a thionyl chloride as a catalyst; and
   (3-7) dissolving a water-soluble unsaturated lipid complex resulting from step (3-6) in water and collecting the water-soluble unsaturated lipid complex using a lyophilizer.

4. The method of claim 1, wherein the oil soluble unsaturated lipid is at least one selected from the group consisting of a fatty acid, a neutral lipid, a fatty acid ester and a steroid.

5. The method of claim 4, wherein the fatty acid is an unsaturated lipid having 10 to 30 carbon atoms and 1 to 6 unsaturated double bonds.

6. The method of claim 5, wherein the fatty acid is at least one selected from the group consisting of a myristoleic acid, a palmitoleic acid, a γ-linolenic acid, an α-linolenic acid, an oleic acid, a linoleic acid, a conjugated linoleic acid, a docosahexaenoic acid(DHA) and an eicosapentaenoic acid(, EPA).

7. The method of claim 1, wherein in step (1-2) the catalyst is a mixture of a pyridine and a thionyl chloride in a ratio of 1:1.

8. The method of claim 2, wherein the emulsifier includes 1.0 to 3.0 weight % of the lecithin, 1.0 to 3.0 weight % of the sucrose fatty acid ester and 0.02 to 0.08 weight % of the ascorbic acid to a total weight of the solution.

9. The method of claim 2, wherein the oil soluble unsaturated lipid is at least one selected from the group consisting of a fatty acid, a neutral lipid, a fatty acid ester and a steroid.

10. The method of claim 9, wherein the fatty acid is an unsaturated lipid having 10 to 30 carbon atoms and 1 to 6 unsaturated double bonds.

11. The method of claim 10, wherein the fatty acid is at least one selected from the group consisting of a myristoleic acid, a palmitoleic acid, a γ-linolenic acid, an α-linolenic acid, an oleic acid, a linoleic acid, a conjugated linoleic acid, a docosahexaenoic acid(DHA) and an eicosapentaenoic acid (EPA).

12. The method of claim 3, wherein the oil soluble unsaturated lipid is at least one selected from the group consisting of a fatty acid, a neutral lipid, a fatty acid ester and a steroid.

13. The method of claim 12, wherein the fatty acid is an unsaturated lipid having 10 to 30 carbon atoms and 1 to 6 unsaturated double bonds.

14. The method of claim 13, wherein the fatty acid is at least one selected from the group consisting of a myristoleic acid, a palmitoleic acid, a γ-linolenic acid, an α-linolenic acid, an oleic acid, a linoleic acid, a conjugated linoleic acid, a docosahexaenoic acid(DHA) and an eicosapentaenoic acid (EPA).

15. The method of claim 3, wherein in step (3-6) the catalyst is a mixture of a pyridine and a thionyl chloride in a ratio of 1:1.

16. The method of claim 3, wherein the emulsifier includes 1.0 to 3.0 weight % of the lecithin, 1.0 to 3.0 weight % of the sucrose fatty acid ester and 0.02 to 0.08 weight % of the ascorbic acid to a total weight of the solution.

17. The method of claim 8, wherein the emulsifier includes 2.0 weight % of the lecithin, 2.0 weight % of the sucrose fatty acid ester and 0.05 weight % of the ascorbic acid to a total weight of the solution.

18. The method of claim 16, wherein the emulsifier includes 2.0 weight of the lecithin, 2.0 weight % of the sucrose fatty acid ester and 0.05 weight % of the ascorbic acid to a total weight of the solution.

19. The method of claim 1, wherein the amino acid is an essential or non-essential amino acid selected from the group consisting of isoleucine, leucine, lysine, phenylalanine, methionine, threonine, tryptophane, valine, alanine, arginine, asparagines, cysteine, glutamine, histidine, proline, serine, tyrosine and glycine.

20. The method of claim 2, wherein the amino acid is an essential or non-essential amino acid selected from the group consisting of isoleucine, leucine, lysine, phenylalanine, methionine, threonine, tryptophane, valine, alanine, arginine, asparagines, cysteine, glutamine, histidine, proline, serine, tyrosine and glycine.

21. The method of claim 3, wherein the amino acid is an essential or non-essential amino acid selected from the group consisting of isoleucine, leucine, lysine, phenylalanine, methionine, threonine, tryptophane, valine, alanine, arginine, asparagines, cysteine, glutamine, histidine, proline, serine, tyrosine and glycine.

22. The method of claim 1, wherein step (1-3) is performed at a temperature of 4° C.

* * * * *